United States Patent
Burkholz et al.

(10) Patent No.: US 10,112,033 B2
(45) Date of Patent: Oct. 30, 2018

(54) INTRAVENOUS NEEDLE ASSEMBLY HAVING BLOOD DISPENSING CAPABILITIES

(71) Applicant: Becton, Dickinson and Company, Franklin Lakes, NJ (US)

(72) Inventors: Jonathan Karl Burkholz, Salt Lake City, UT (US); J'Lynn Ingleby, Sandy, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 438 days.

(21) Appl. No.: 14/326,078

(22) Filed: Jul. 8, 2014

(65) Prior Publication Data

US 2016/0008579 A1 Jan. 14, 2016

(51) Int. Cl.
*A61M 5/178* (2006.01)
*A61M 25/06* (2006.01)
(Continued)

(52) U.S. Cl.
CPC ..... *A61M 25/0606* (2013.01); *A61B 5/15003* (2013.01); *A61B 5/153* (2013.01);
(Continued)

(58) Field of Classification Search
CPC .... A61M 5/158; A61M 5/162; A61M 5/3129; A61M 5/31511; A61M 5/1626; A61M 25/0618; A61M 5/06; A61M 5/31551; A61M 3/0262; A61M 11/008; A61M 5/282; A61M 5/2425; A61M 5/321; A61M 5/3243; A61M 25/0631; A61M 5/0606; A61M 5/0625; A61M 5/0618; A61B 17/3494; A61B 5/150213; A51M 25/06;
(Continued)

(56) References Cited

U.S. PATENT DOCUMENTS 4,172,448 A 10/1979 Brush
4,703,761 A 11/1987 Rathbone et al.
(Continued)

FOREIGN PATENT DOCUMENTS

EP 0812601 A2 12/1997
EP 1132103 A1 9/2001
(Continued)

*Primary Examiner* — Kevin C Sirmons
*Assistant Examiner* — Tiffany Legette-Thompson
(74) *Attorney, Agent, or Firm* — Kevin Stinger; Craig Metcalf; Kirton McConkie

(57) ABSTRACT

A needle assembly can include a needle and a proximal compartment forming a reservoir for collecting blood that flows through an inner lumen of needle. The needle assembly may also include a needle tip shield for capturing a sharpened distal tip of the needle. The needle tip shield can form a fluid pathway through which blood contained within the reservoir is expelled. The volume of the reservoir can be reduced to cause blood to be expelled from the needle tip shield such as by compressing the proximal compartment or a plunger connected to the proximal compartment or by moving a plunger into the reservoir. The fluid pathway of the needle tip shield can either be the same pathway through which the sharpened distal tip is withdrawn into the needle tip shield, or can be a separate pathway.

13 Claims, 14 Drawing Sheets

(51) Int. Cl.
  *A61B 5/15* (2006.01)
  *A61B 5/153* (2006.01)
  *A61M 5/158* (2006.01)
  *A61M 5/162* (2006.01)
  *A61M 5/31* (2006.01)
  *A61M 5/315* (2006.01)

(52) U.S. Cl.
  CPC .. *A61B 5/150404* (2013.01); *A61B 5/150519* (2013.01); *A61B 5/150633* (2013.01); *A61M 5/158* (2013.01); *A61M 5/1626* (2013.01); *A61M 25/0618* (2013.01); *A61M 25/0625* (2013.01); *A61B 5/150213* (2013.01); *A61B 5/150992* (2013.01); *A61M 5/3129* (2013.01); *A61M 5/31511* (2013.01); *A61M 2005/1587* (2013.01)

(58) Field of Classification Search
  CPC .......... A51M 25/0606; A51M 25/0625; A51M 25/0618
  USPC ........... 604/164.08, 212, 275, 162, 198, 228
  See application file for complete search history.

(56) References Cited

U.S. PATENT DOCUMENTS

| | | |
|---|---|---|
| 4,772,264 A | 9/1988 | Cragg |
| 5,049,136 A * | 9/1991 | Johnson ................ A61M 5/326 604/198 |
| 5,215,529 A | 6/1993 | Fields et al. |
| 5,542,932 A | 8/1996 | Daugherty |
| 5,601,536 A | 2/1997 | Crawford et al. |
| 5,702,383 A | 12/1997 | Giesler et al. |
| 5,800,399 A | 9/1998 | Bogert et al. |
| 5,833,670 A | 11/1998 | Dillon et al. |
| 5,899,889 A * | 5/1999 | Futagawa ........... A61M 5/2425 604/218 |
| 6,004,294 A | 12/1999 | Brimhall et al. |
| 6,117,108 A | 9/2000 | Woehr et al. |
| 6,379,333 B1 | 4/2002 | Brimhall et al. |
| 6,443,927 B1 | 9/2002 | Cook |
| 6,616,630 B1 | 9/2003 | Woehr et al. |
| 6,629,959 B2 | 10/2003 | Kuracina et al. |
| 6,652,490 B2 | 11/2003 | Howell |
| 6,692,471 B2 | 2/2004 | Boudreaux |
| 6,749,588 B1 | 6/2004 | Howell et al. |
| 6,860,871 B2 | 3/2005 | Kuracina et al. |
| 7,160,269 B2 | 1/2007 | Woehr |
| 7,186,239 B2 | 3/2007 | Woehr |
| 7,264,613 B2 | 9/2007 | Woehr et al. |
| 7,488,297 B2 | 2/2009 | Flaherty |
| 8,383,044 B2 | 2/2013 | Davis et al. |
| 8,496,623 B2 | 7/2013 | Burkholz |
| 8,597,252 B2 | 12/2013 | Burkholz et al. |
| 2003/0072676 A1 | 4/2003 | Fletcher-Haynes et al. |
| 2004/0116830 A1 | 6/2004 | Trudeau et al. |
| 2004/0243061 A1 | 12/2004 | McGurk |
| 2005/0101920 A1* | 5/2005 | Keane ................ A61B 5/15003 604/218 |
| 2006/0253087 A1* | 11/2006 | Vlodaver ................ A61F 11/00 604/275 |
| 2007/0191777 A1 | 8/2007 | King |
| 2008/0108944 A1* | 5/2008 | Woehr ................ A61B 5/1411 604/164.08 |
| 2008/0255473 A1 | 10/2008 | Dalebout et al. |
| 2009/0099431 A1 | 4/2009 | Dalebout et al. |
| 2009/0198194 A1* | 8/2009 | Madin ................ A61M 5/3148 604/218 |
| 2011/0009717 A1* | 1/2011 | Davis ................... A61B 5/1405 600/309 |
| 2011/0046555 A1* | 2/2011 | Abe ....................... A61M 5/158 604/164.08 |
| 2012/0016265 A1 | 1/2012 | Peterson et al. |
| 2012/0016307 A1 | 1/2012 | Burkholz et al. |
| 2012/0116436 A1 | 5/2012 | Wiegel |
| 2013/0310751 A1 | 11/2013 | Davis et al. |
| 2014/0135652 A1 | 5/2014 | Wilkinson |

FOREIGN PATENT DOCUMENTS

| | | |
|---|---|---|
| EP | 1884257 A1 | 2/2008 |
| WO | 0112254 A1 | 2/2001 |

* cited by examiner

INTRAVENOUS NEEDLE ASSEMBLY HAVING BLOOD DISPENSING CAPABILITIES

BACKGROUND OF THE INVENTION

The present invention relates generally to intravenous needle assemblies that include blood dispensing capabilities. In particular, the present invention discloses intravenous needle assemblies that can be used to dispense small amounts of blood for point-of-care testing or other testing that requires a small but controlled amount of blood.

Intravenous devices such as catheters oftentimes include a needle that employs a needle tip shield. These needle tip shields are configured to cover the needle tip once the needle has been withdrawn from the device, such as, for example, when the needle is withdrawn from a catheter adapter. Once actuated, a needle tip shield secures the needle tip within the needle shield thereby preventing accidental stickings.

BRIEF SUMMARY OF THE INVENTION

The present invention extends to needle assemblies and intravenous devices, such as peripheral intravenous catheters, that include needle assemblies that have blood dispensing capabilities. A needle assembly can include a needle and a proximal compartment forming a reservoir for collecting blood that flows through an inner lumen of the needle. The proximal compartment may be in communication with a vent to facilitate blood flow into the proximal compartment. The needle assembly may also include a needle tip shield for capturing a sharpened distal tip of the needle. The needle tip shield can form a fluid pathway through which blood contained within the reservoir is expelled. The volume of the reservoir can be reduced to cause blood to be expelled from the needle tip shield such as by compressing the proximal compartment or a plunger connected to the proximal compartment or by moving a plunger into the reservoir. The fluid pathway of the needle tip shield can either be the same pathway through which the sharpened distal tip is withdrawn into the needle tip shield, or can be a separate pathway.

In one embodiment, the present invention is implemented as a needle assembly that includes a needle having a sharpened distal tip and an inner lumen. The needle is configured to be used within an intravenous device. The needle assembly also includes a proximal compartment secured to a proximal end of the needle. The proximal compartment forms a reservoir that is in fluid communication with the inner lumen of the needle thereby allowing blood to be withdrawn through the inner lumen and into the reservoir. The needle assembly further includes a needle tip shield secured to the needle and configured to capture the sharpened distal tip when the sharpened distal tip is withdrawn from the intravenous device. The needle tip shield forms a fluid pathway for dispensing blood contained within the reservoir.

The proximal compartment may be compressible or may include a plunger to reduce the volume of the reservoir thereby causing blood to be expelled through the needle tip shield. The plunger may also include a reservoir and may be removable from the proximal compartment to enable blood contained within the plunger's reservoir to be expelled through an opening of the plunger. The plunger may be compressible or may also include a plunger for reducing the volume of the plunger's reservoir. The proximal compartment may include a seal for sealing the reservoir when the plunger is removed.

The fluid pathway of the needle tip shield may be the same pathway through which the sharpened distal tip is withdrawn into the needle tip shield or may be a different pathway. The fluid pathway may include a narrowed inner diameter that prevents blood flow from the fluid pathway without a reduction to the volume of the reservoir of the proximal compartment. The narrowed inner diameter may be formed at a distal opening of the fluid pathway or may be formed by a separate component that enters the fluid pathway when the sharpened distal tip is withdrawn into the needle tip shield. The separate component may prevent the sharpened distal tip from emerging distally from the needle tip shield.

In another embodiment, the present invention is implemented as an intravenous catheter that includes a catheter adapter from which a catheter extends, and a needle having a sharpened distal tip and an inner lumen. The needle extends through the catheter adapter and the catheter such that the sharpened distal tip extends distally from the catheter. The intravenous device also includes a proximal compartment secured to a proximal end of the needle. The proximal compartment extends proximally from the catheter adapter and forms a reservoir for collection of blood via the inner lumen of the the needle. The intravenous device further includes a needle tip shield secured to the needle and configured to capture the sharpened distal tip when the sharpened distal tip is withdrawn from the catheter adapter. The needle tip shield forms a fluid pathway for dispensing blood contained within the reservoir when the needle is removed from the catheter adapter.

The fluid pathway may be configured to prevent blood flow from the reservoir without a reduction in the volume of the reservoir. The proximal compartment may either be compressible or include a plunger that is moveable into the reservoir for reducing the volume of the reservoir. The fluid pathway may either be the same pathway through which the sharpened distal tip is withdrawn into the needle tip shield, or a different pathway than a pathway through which the sharpened distal tip is withdrawn into the needle tip shield.

In another embodiment, the present invention is implemented as a needle assembly that includes a needle having a sharpened distal tip and an inner lumen, and a proximal compartment forming a reservoir that is in fluid communication with the inner lumen of the needle for collection of blood via the inner lumen of the the needle. The needle assembly also includes a needle tip shield configured to capture the sharpened distal tip after the sharpened distal tip has been used to access a patient's vasculature. The needle tip shield forms a fluid pathway for dispensing blood contained within the reservoir. The volume of the reservoir is reduced to cause blood contained within the reservoir to be expelled through the fluid pathway of the needle tip shield.

The volume of the reservoir may be reduced by compressing a portion of the proximal compartment, advancing a plunger into the reservoir, and/or compressing a plunger having a second reservoir that is in fluid communication with the reservoir. The needle tip shield may include a pathway through which the sharpened distal tip is withdrawn into the needle tip shield, and the fluid pathway may be the same pathway through which the sharpened distal tip is withdrawn into the needle tip shield, or a different pathway than the pathway through which the sharpened distal tip is withdrawn into the needle tip shield.

This summary is provided to introduce a selection of concepts in a simplified form that are further described below in the Detailed Description. This Summary is not intended to identify key features or essential features of the claimed subject matter.

Additional features and advantages of the invention will be set forth in the description which follows, and in part will be obvious from the description, or may be learned by the practice of the invention. The features and advantages of the invention may be realized and obtained by means of the instruments and combinations particularly pointed out in the appended claims. These and other features of the present invention will become more fully apparent from the following description and appended claims, or may be learned by the practice of the invention as set forth hereinafter.

BRIEF DESCRIPTION OF THE DRAWINGS

In order to describe the manner in which the above-recited and other advantages and features of the invention can be obtained, a more particular description of the invention briefly described above will be rendered by reference to specific embodiments thereof which are illustrated in the appended drawings. Understanding that these drawings depict only typical embodiments of the invention and are not therefore to be considered to be limiting of its scope, the invention will be described and explained with additional specificity and detail through the use of the accompanying drawings in which.

DETAILED DESCRIPTION OF THE INVENTION

Figure 1A:
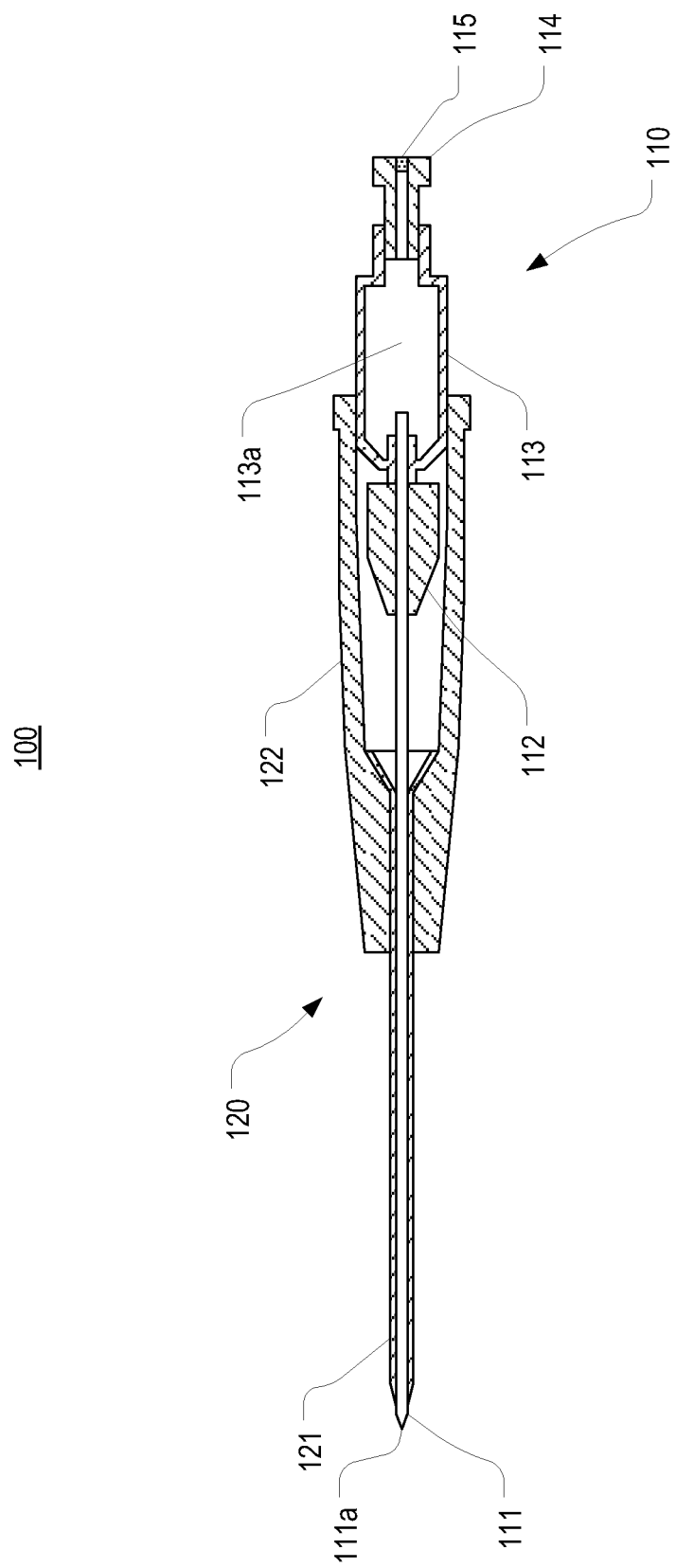
FIGS. 1A-1D illustrate cross-sectional front views of an intravenous device that includes a needle assembly having blood dispensing capabilities in accordance with one or more embodiments of the invention.

The present invention extends to needle assemblies and intravenous devices, such as peripheral intravenous catheters, that include needle assemblies that have blood dispensing capabilities. The blood dispensing capabilities can be provided by employing a proximal compartment that forms a reservoir for collecting blood that flows through an inner lumen of needle. A needle tip shield for capturing a sharpened distal tip of the needle can form a fluid pathway through which blood contained within the reservoir is expelled.

In this specification, a fluid pathway should be construed as any opening through a component that allows blood to move from the bore of a needle out through the opening. As an example, a fluid pathway can be formed in a needle tip shield to allow blood to flow from the bore of a needle contained within the needle tip shield out from the needle tip shield. A pathway can include a fluid pathway as well as a pathway through which the needle is moved, but through which blood does not flow.

The volume of the reservoir can be reduced to cause blood to be expelled from the needle tip shield. This reduction of the volume can be accomplished by compressing a portion of the proximal compartment, compressing a plunger connected to the proximal compartment, or by moving a plunger into the reservoir. The fluid pathway of the needle tip shield can either be the same pathway through which the sharpened distal tip is withdrawn into the needle tip shield, or can be a separate pathway.

The figures provide various examples of intravenous devices that can include a needle assembly with blood dispensing capabilities in accordance with embodiments of the present invention. In each of the figures, a peripheral intravenous catheter is depicted as the intravenous device. However, any other type of intravenous device that employs a needle for vascular access could be configured to include a needle assembly with blood dispensing capabilities in accordance with one or more embodiments of the present invention.

FIGS. 1A-1D illustrate cross-sectional front views of an intravenous device 100 that includes a needle assembly configured in accordance with one or more embodiments of the present invention. Intravenous device 100 includes a needle assembly 110 and a catheter assembly 120. Catheter assembly 120 is generally comprised of a catheter adapter 122 from which a catheter 121 extends distally. Needle assembly 110 includes a needle 111, a needle tip shield 112, and a proximal compartment 113. Needle 111 can have any gauge or length suitable for vascular access. A distal tip 111a of needle 111 is typically sharpened to facilitate penetration through the skin of a patient.

Needle tip shield 112, for ease of illustration, is shown as a single unitary component through which needle 111 extends prior to needle tip shield 112 being actuated to cover the distal tip of needle 111. However, may different types of needle tip shields could be employed in embodiments of the present invention. For example, a needle tip shield could include multiple components that move with respect to one another and are interconnected in some manner such as via a spring or other biasing means. At a minimum, a needle tip shield suitable for use in the present invention should be capable of covering the distal tip of the needle to prevent accidental sticking after the needle has been used to access a patient's vasculature, and should provide a fluid pathway for dispensing blood collected via the needle during vascular access as will be further described below.

Proximal compartment 113 comprises a reservoir 113a that is in fluid communication with an inner lumen of needle 111. Accordingly, when distal tip 111a is positioned within a patient's vasculature, such as is shown in FIG. 1B, blood 150 can flow through the inner lumen and collect within reservoir 113a. To facilitate blood flow into reservoir 113a, proximal compartment 113 can include a vent 115. Typically, the vent can be permeable to air but not blood. A vent can be formed anywhere on proximal compartment 113 as long as the vent is exposed to reservoir 113a, including being formed on or in a separate component that is attached to proximal compartment 113. For example, in the embodiment shown in FIGS. 1A-1D, a vent 115 is formed in a plunger 114 that extends into proximal compartment 113. Plunger, as used in this specification, refers to a component that is moveable within another component to cause the volume of a reservoir to be reduced. A plunger may, but is not required to be, removable from the component within which it is moveable.

Figure 1B:
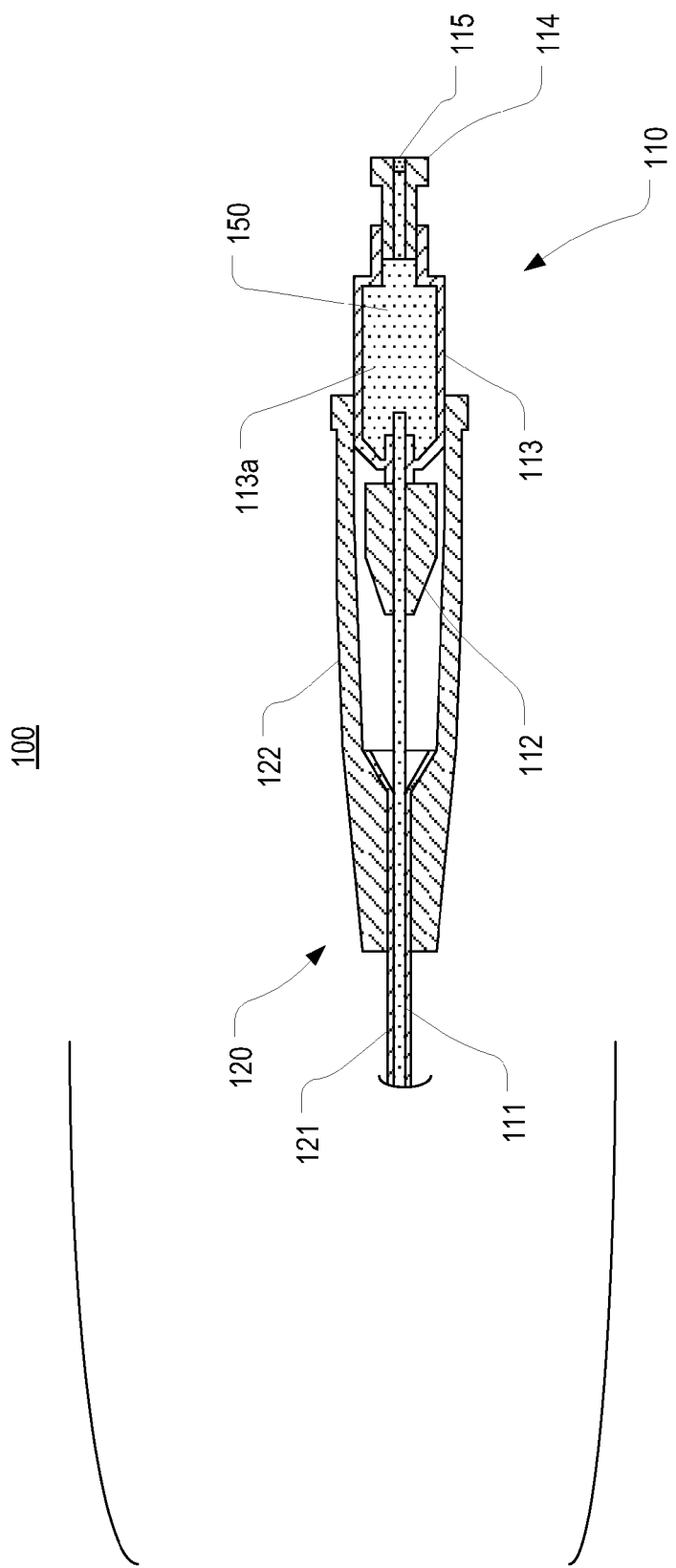

Although FIGS. 1A and 1B illustrate that proximal compartment 113 inserts partially into the proximal end of catheter adapter 122, in other designs, proximal compartment 113 may not extend into catheter adapter 122. For example, proximal compartment 113 may abut a proximal surface of catheter adapter 122 or may extend overtop a portion of catheter adapter 122. In some embodiments, proximal compartment 113 can comprise a needle hub (or other grip) for needle 111 that the clinician holds during withdrawal of needle 111 from catheter assembly 120. In other embodiments, proximal compartment 113 can be separate from a needle hub. For example, proximal compartment 113 can be positioned proximally or distally to a needle hub of needle 111.

Figure 1C:
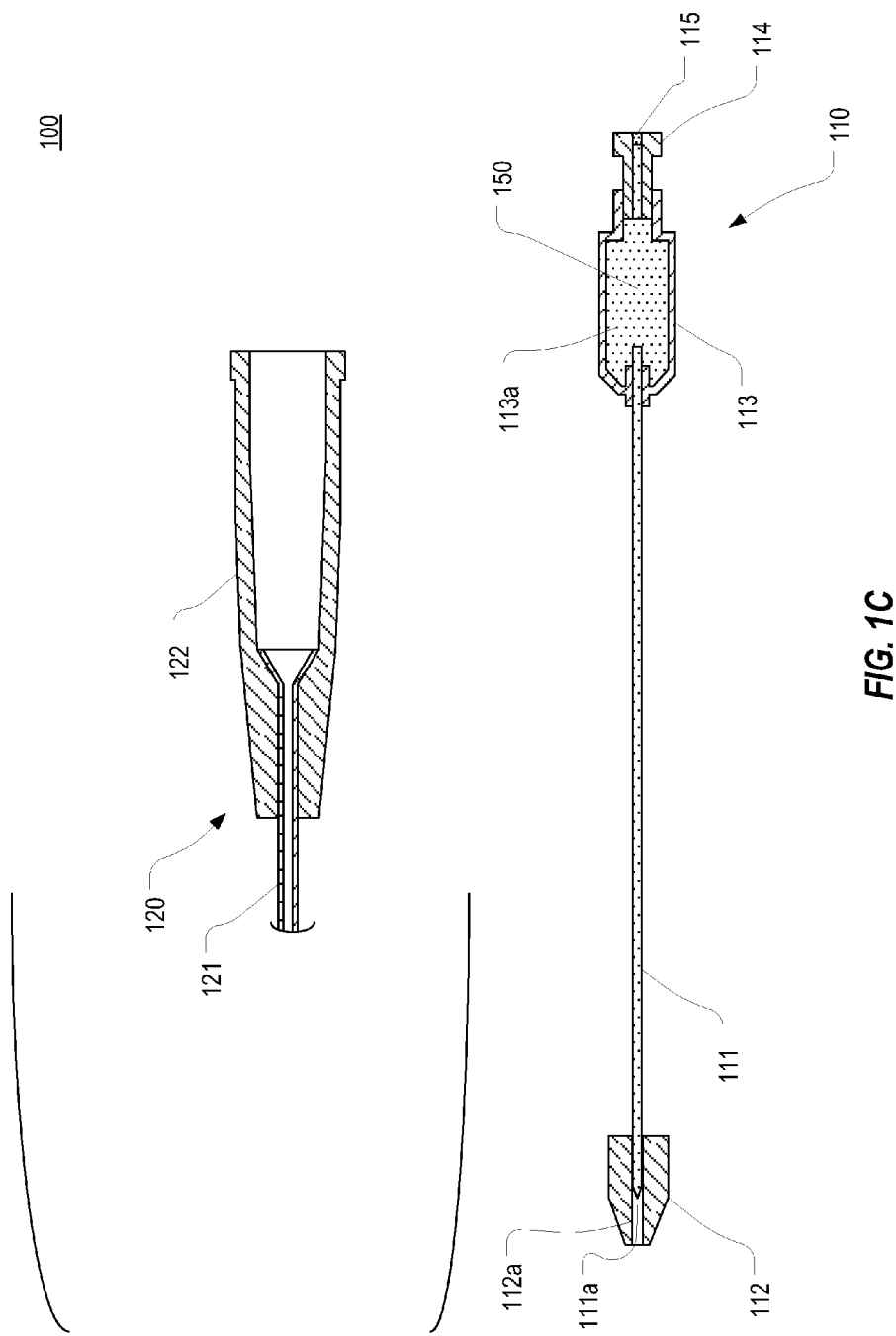

As shown in FIG. 1C, once catheter 121 has been appropriately positioned within the patient's vasculature, needle assembly 110 can be removed from catheter assembly 120. When needle 111 is withdrawn from catheter assembly 120, needle tip shield 112 can be actuated to capture distal tip 111a within the needle tip shield. Although not depicted in the figures, needle tip shield 112 and/or catheter adapter 122 can interact in some manner to ensure that distal tip 111a cannot be withdrawn from catheter adapter 122 without first actuating needle tip shield 112 as is known in the art.

FIG. 1C illustrates that needle tip 111a is positioned within a pathway 112a of needle tip shield 112. Although not depicted, needle tip shield 112 may be configured with various structures that prevent distal tip 111a from reemerging from the distal end of needle tip shield 112. The particular manner in which distal tip 111a is prevented from reemerging is not essential to the invention, and therefore, for ease of illustration, FIGS. 1A-1D do not depict any structure for securing distal tip 111a within needle tip shield 112.

Of importance to the invention, needle tip shield 112 includes a fluid pathway 112a through which blood 150 contained within proximal compartment 113 can be expelled. Fluid pathway 112a, in some embodiments such as is shown in FIGS. 1A-1D, can be the same pathway through which distal tip 111a is withdrawn into needle tip shield 112. In other embodiments, fluid pathway 112a can be a different pathway from the pathway through which distal tip 111a is withdrawn into needle tip shield 112.

Whether fluid pathway 112a is the same or different pathway used to withdraw distal tip 111a into needle tip shield 112, fluid pathway 112a can be configured to prevent the flow of blood 150 out from needle tip shield 112 absent a reduction in the volume of reservoir 113a. For example, fluid pathway 112a can have a reduced inside diameter that creates sufficient surface tension to retain blood 150 within fluid pathway 112a.

Figure 1D:
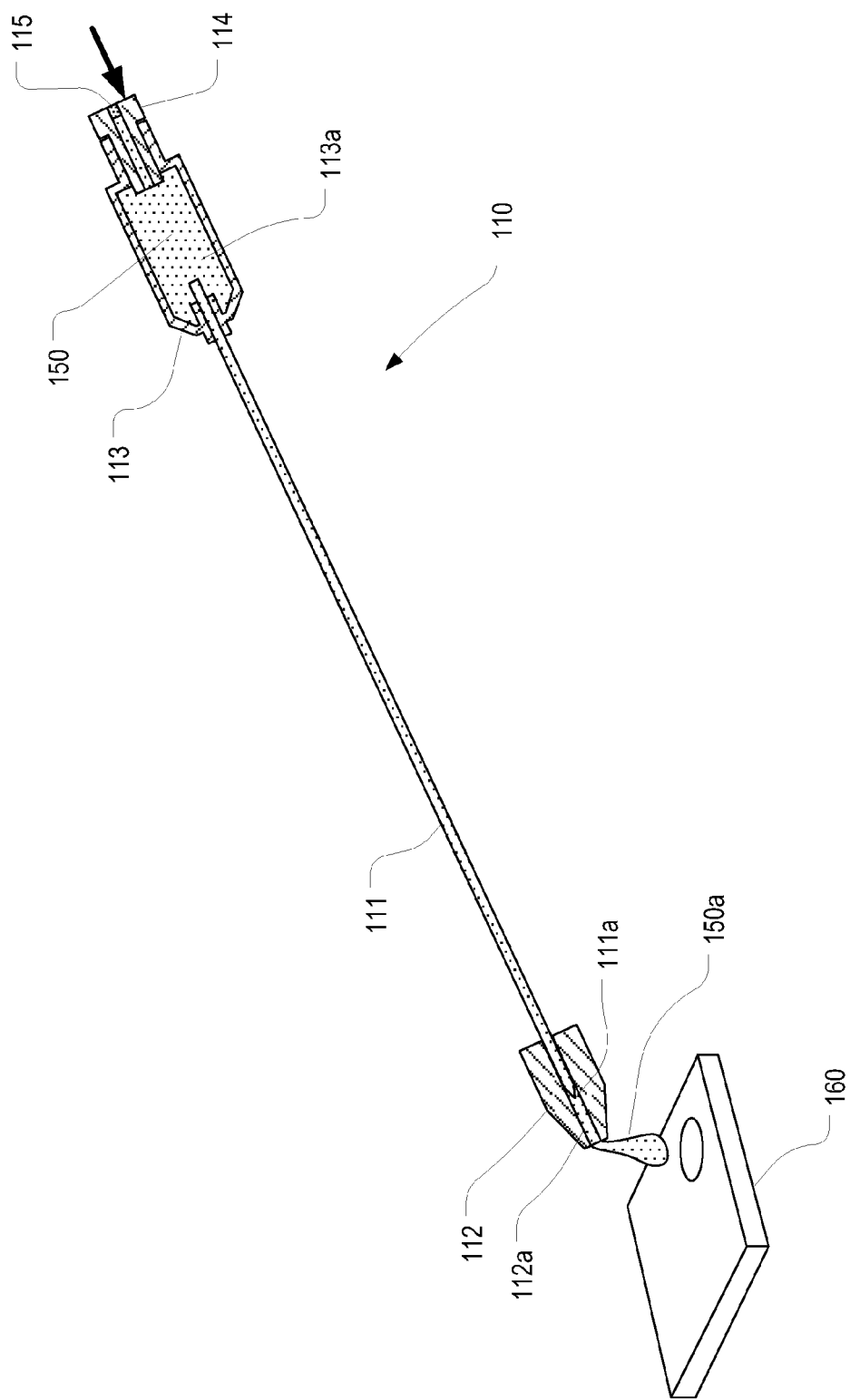

In the embodiment depicted in FIGS. 1A-1D, proximal compartment 113 includes a plunger 114 that is moveable into reservoir 113a thereby reducing the volume of reservoir 113a. Plunger 114 includes a vent 115 to facilitate blood flow into proximal compartment 113. This movement of plunger 114 into reservoir 113a will therefore cause blood 150 to be expelled from needle tip shield 112. As shown in FIG. 1D, plunger 114 has been moved further into proximal compartment 113 reducing the volume of reservoir 113a and causing blood 150a to flow out of fluid pathway 112a onto the surface of a point-of-care cartridge 160. Preferably, plunger 114 can be moved without first removing the plunger from proximal compartment 113. Accordingly, the present invention can facilitate point-of-care testing using blood obtained by a needle during insertion of a catheter.

Although not depicted in FIGS. 1A-1D, proximal compartment 113 may also be compressible to facilitate expelling blood 150 through fluid pathway 112a. In some embodiments, plunger 114 can be employed to enable dispensing of a precise amount of blood. For example, plunger 114 can be initially positioned so that, once it is fully inserted into proximal compartment 113, a precise amount of blood will be expelled. In other embodiments, plunger 114 may include ribs, lines, or other markings that identify how much blood will be expelled by inserting the plunger up to a particular line. Such precision can facilitate use of the present invention for dispensing blood when a precise amount is required.

Figure 2A:
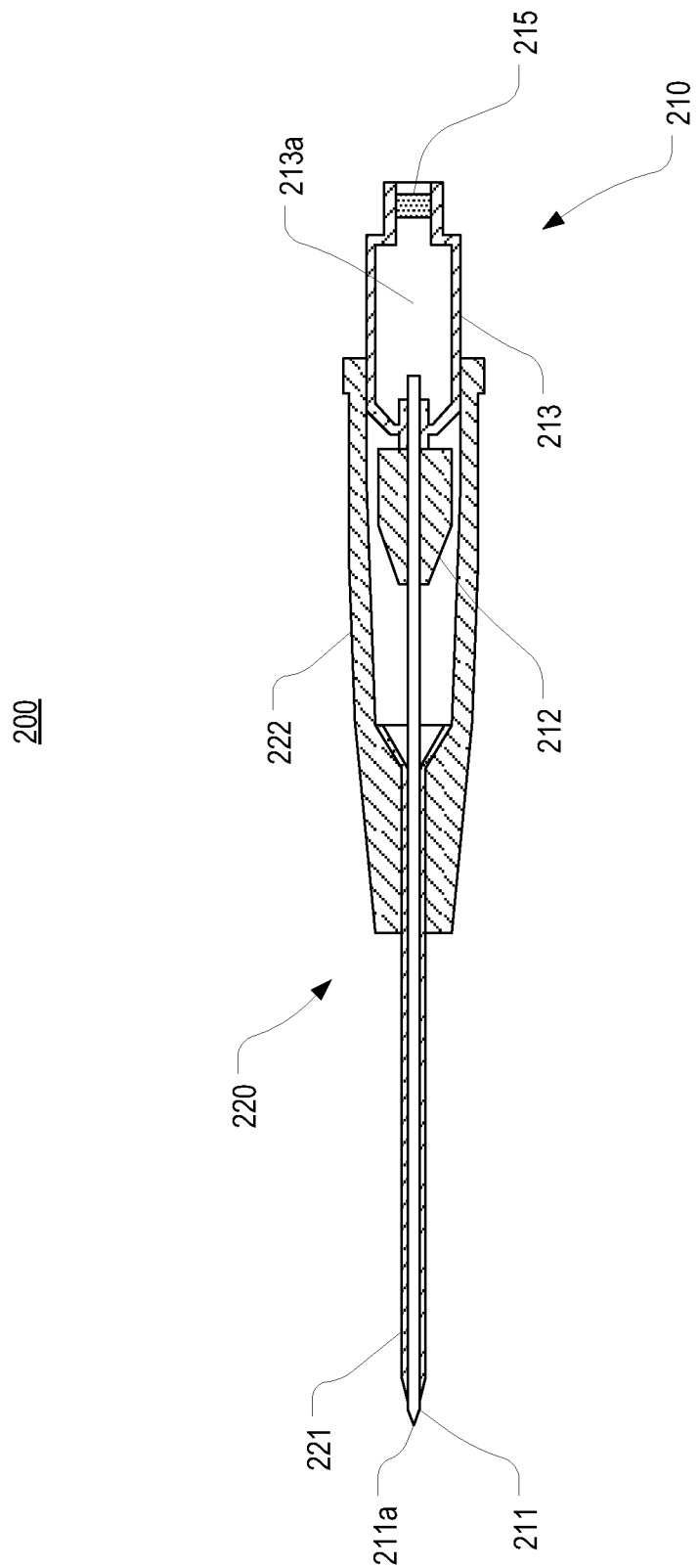
FIGS. 2A and 2B illustrate cross-sectional front views of another intravenous device that includes a needle assembly having blood dispensing capabilities in accordance with one or more embodiments of the invention.
Figure 2B:
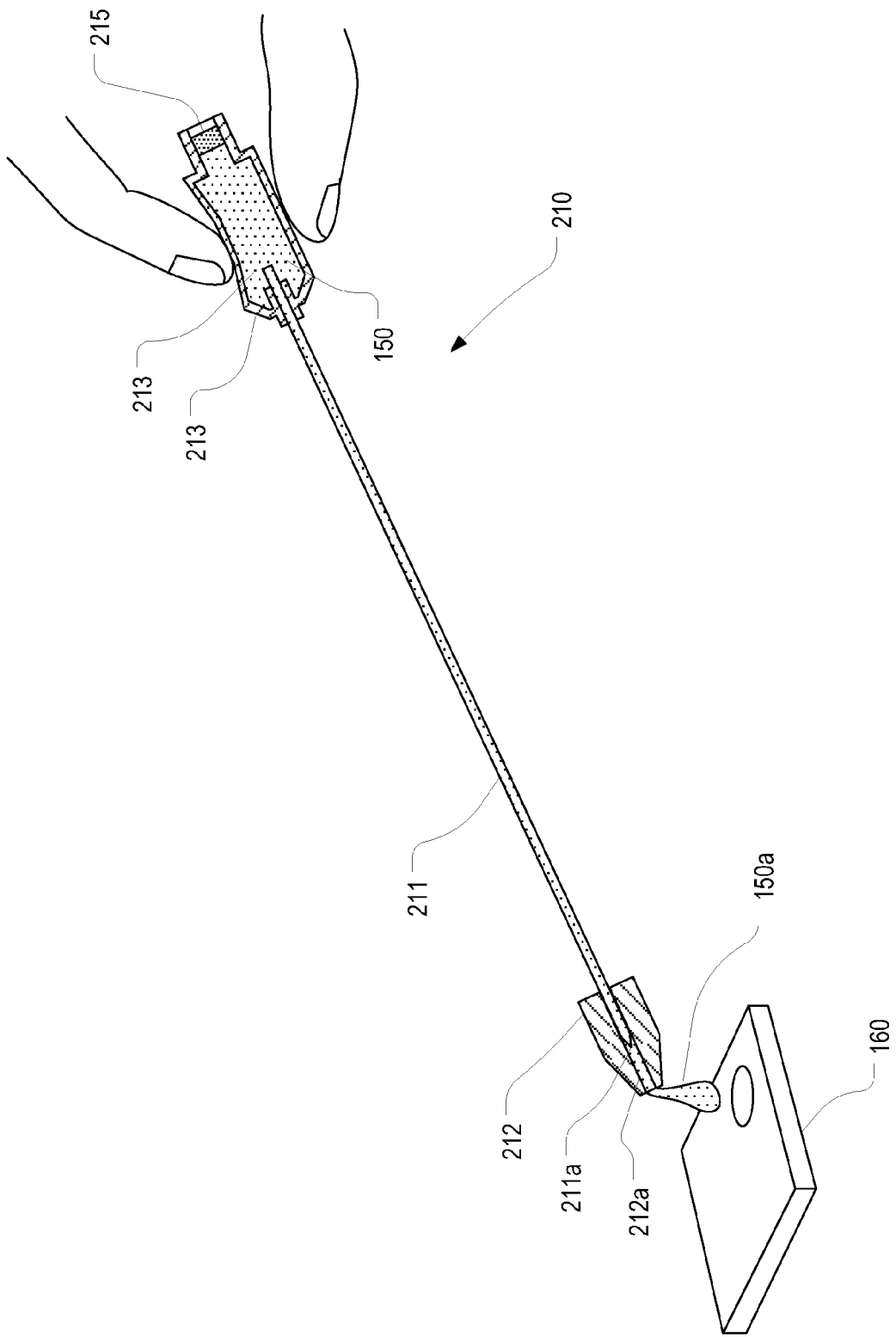

FIGS. 2A and 2B illustrate cross-sectional front views of another intravenous device 200 that includes a needle assembly configured in accordance with one or more embodiments of the present invention. Intravenous device 200 is substantially similar to intravenous device 100 except that proximal compartment 213 does not include a plunger. Instead, proximal compartment 213, or at least a portion of proximal compartment 213, is compressible to cause the volume of reservoir 213a to be reduced as shown in FIG. 2B. To facilitate blood flow into reservoir 213a, proximal compartment 213 can include a vent 215 that is permeable to air, but not blood.

FIGS. 3A-3F illustrate cross-sectional front views of another intravenous device 300 that includes a needle assembly configured in accordance with one or more embodiments of the present invention. Intravenous device 300 is substantially similar to intravenous device 100 except that proximal compartment 313 includes a plunger 314 having a second reservoir 314a. Plunger 314 can include a vent 315 for facilitating blood flow into reservoirs 313a and 314a.

Figure 3A:
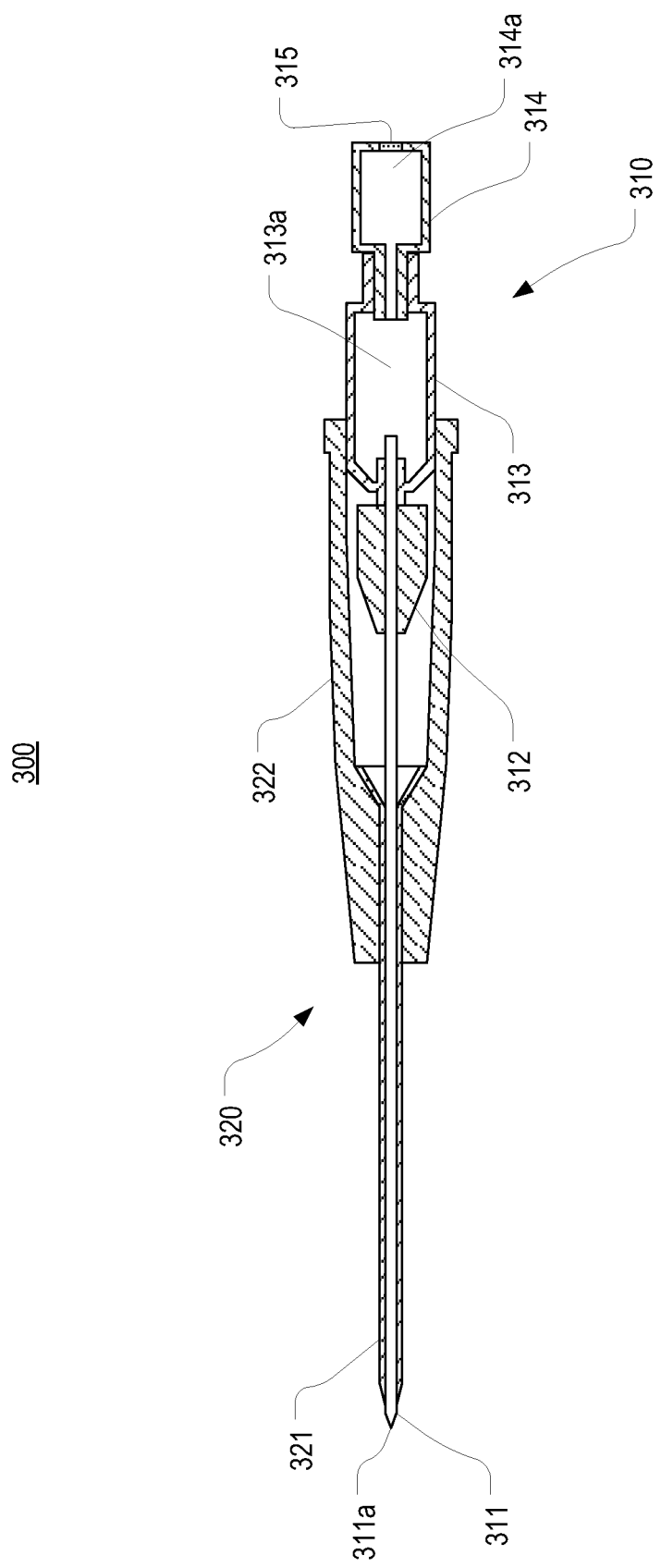
FIGS. 3A-3F illustrate cross-sectional front views of another intravenous device that includes a needle assembly having blood dispensing capabilities in accordance with one or more embodiments of the invention.
Figure 3B:
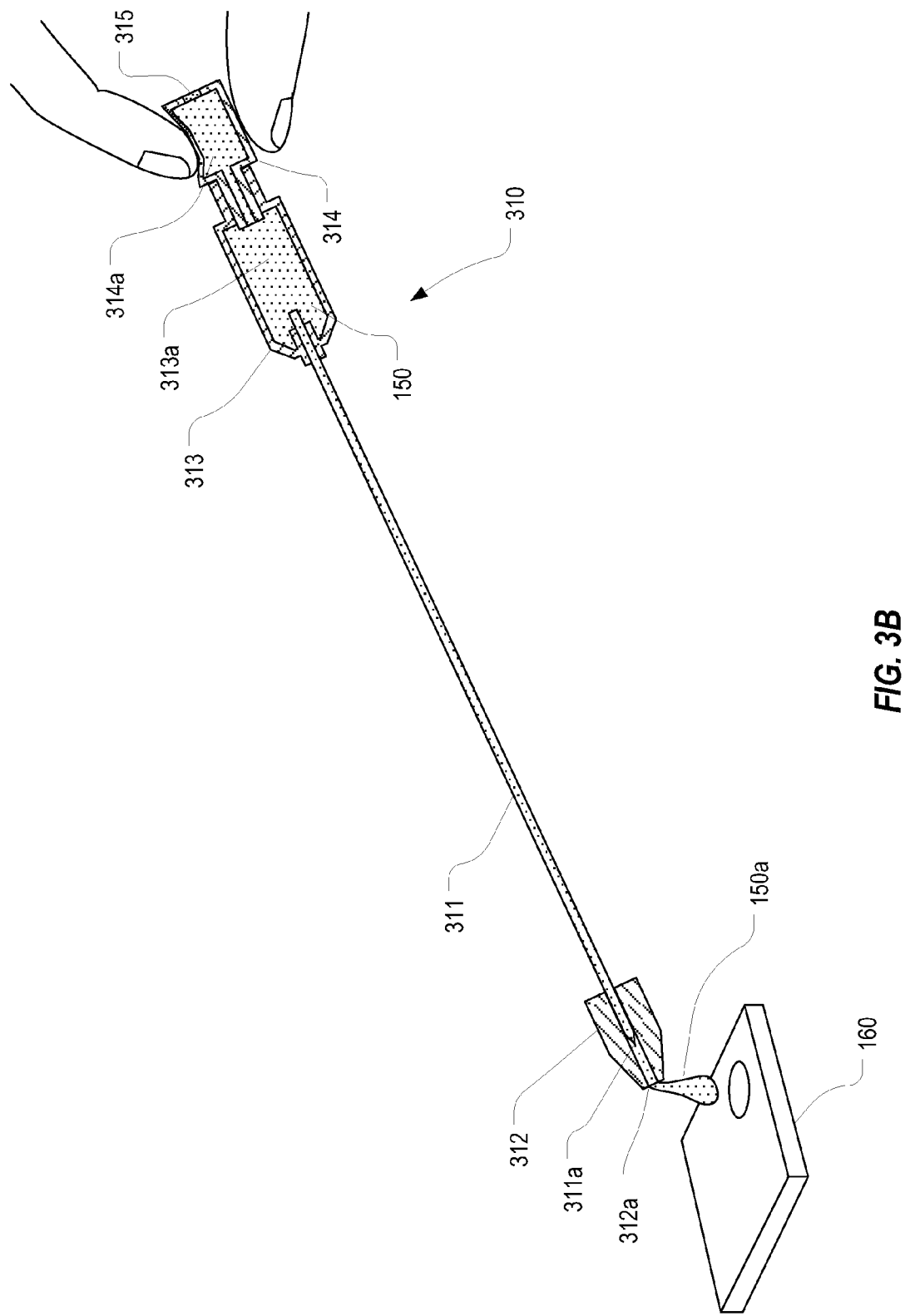

As shown in FIG. 3B, plunger 314, or at least a portion of plunger 314, can be compressible to cause blood 150 to flow out from fluid pathway 312a in needle tip shield 312. In some embodiments, proximal compartment 313 may alternatively or additionally be compressible. Accordingly, one or both of proximal compartment 313 and plunger 314 may be compressible to cause blood 150 to be expelled from fluid pathway 312a.

Figure 3C:
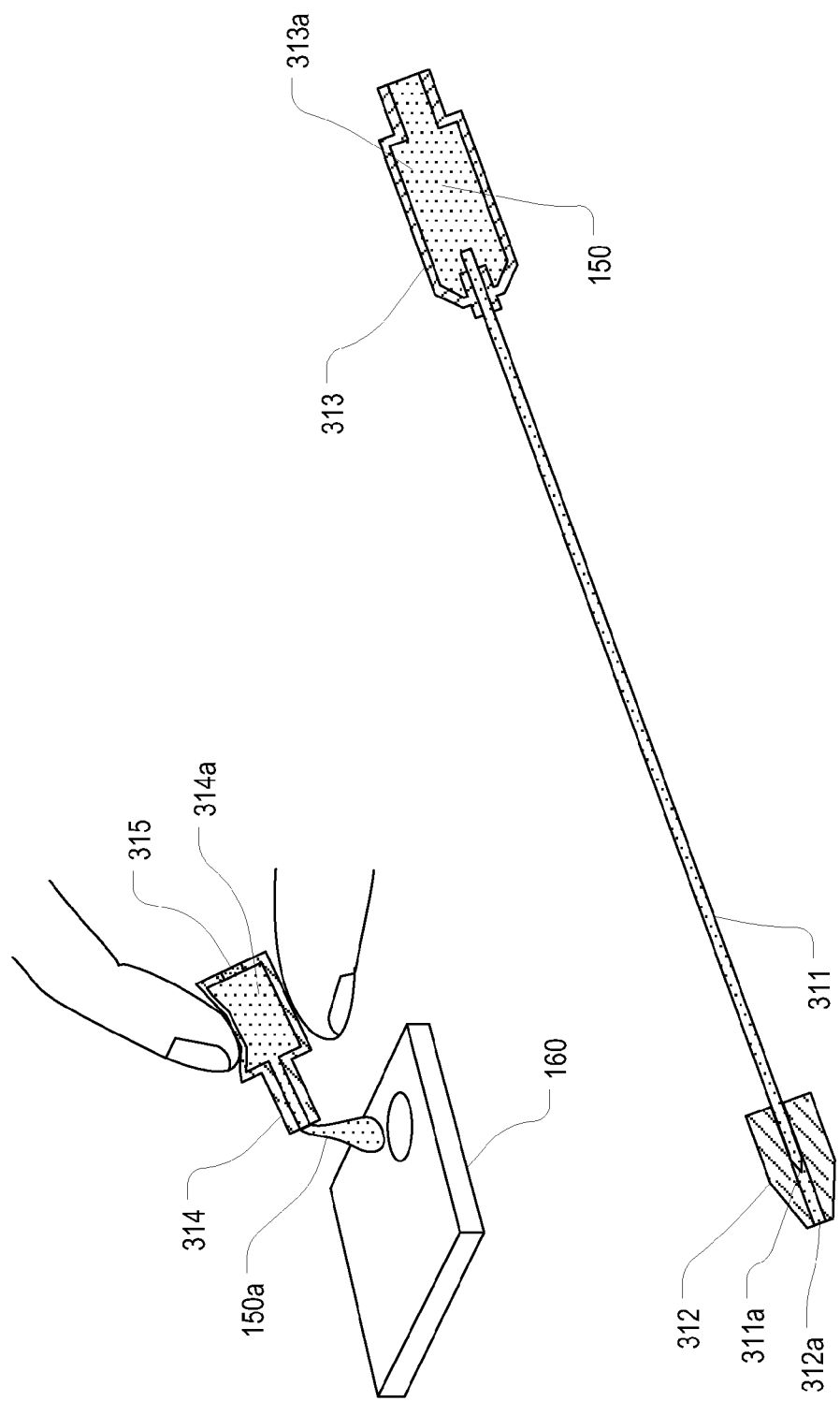

In some embodiments, as is shown in FIG. 3C, plunger 314 may be removable from proximal compartment 313. In this way, plunger 314 can be used to independently expel blood 150a such as on a point-of-care test cartridge 160 as shown. In such embodiments, plunger 314 can be compressible to facilitate expelling blood. To prevent blood flow from reservoir 314a absent compression of plunger 314, plunger 314 may be configured with a reduced sized opening.

Figure 3D:
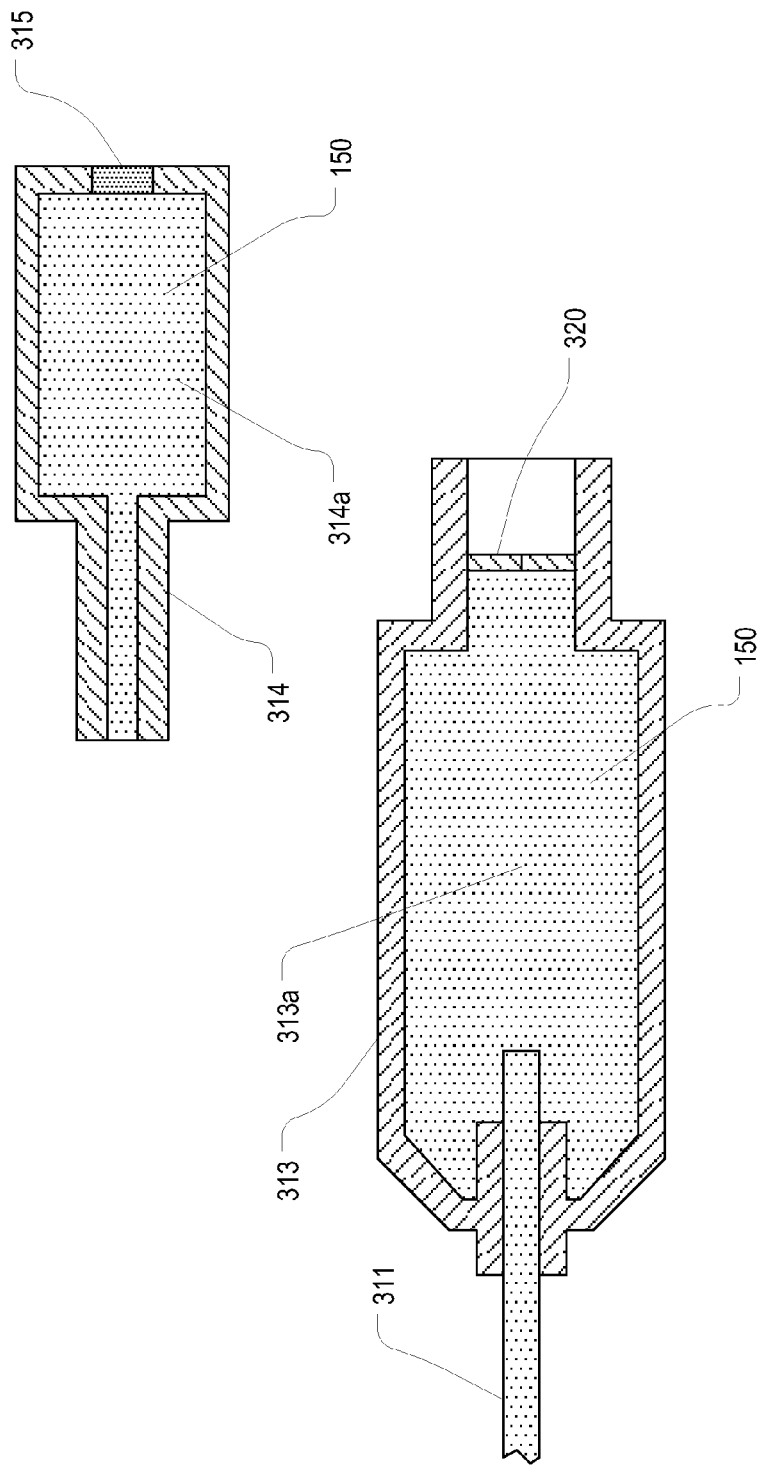

In embodiments where plunger 314 is removable, proximal compartment 313 may include a seal 320 as shown in FIG. 3D. Seal 320 can be configured to be bypassed by a distal tip of plunger 314 when plunger 314 is connected to proximal compartment 313, and then to reseal once plunger 314 is removed. For example, seal 320 can be formed using an elastomeric septum or other structure.

Figure 3E:
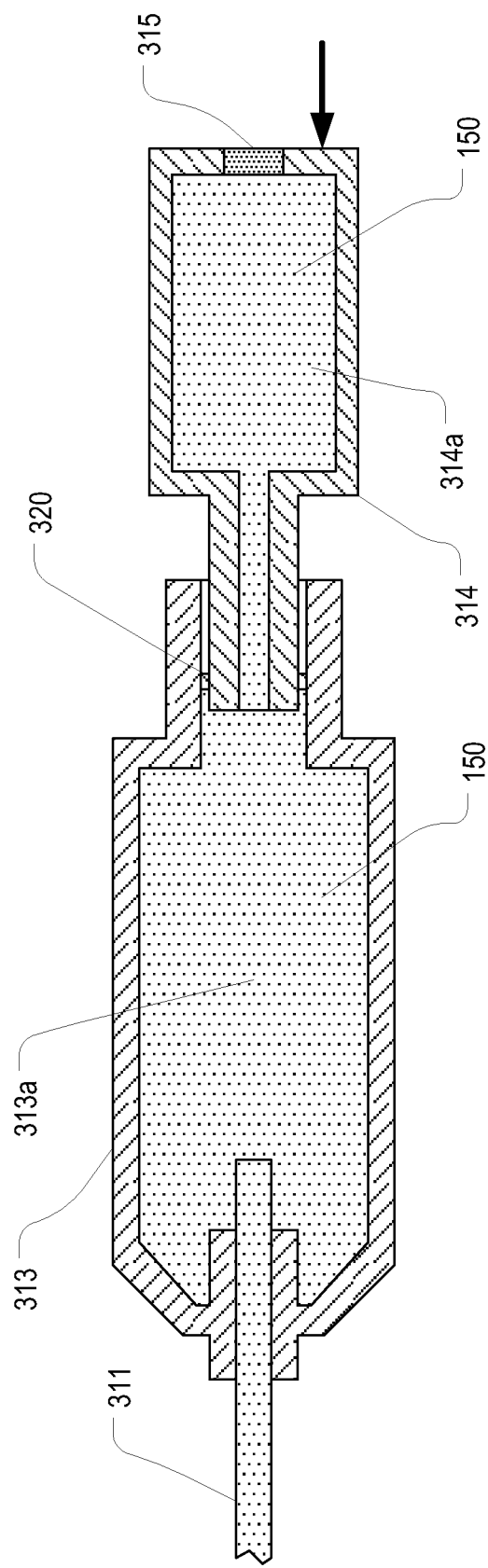

As shown in FIG. 3E, in some embodiments, plunger 314 can initially be positioned so that it may be forced into reservoir 313a as described above with respect to FIG. 1D. In such embodiments, plunger 314 and/or proximal compartment 313 may be compressible, and plunger 314 may be removable. Also, plunger 314 may include ribs, lines, or other markings for identifying an amount of blood that will be expelled when plunger 314 is inserted up to a particular line as described above.

Figure 3F:
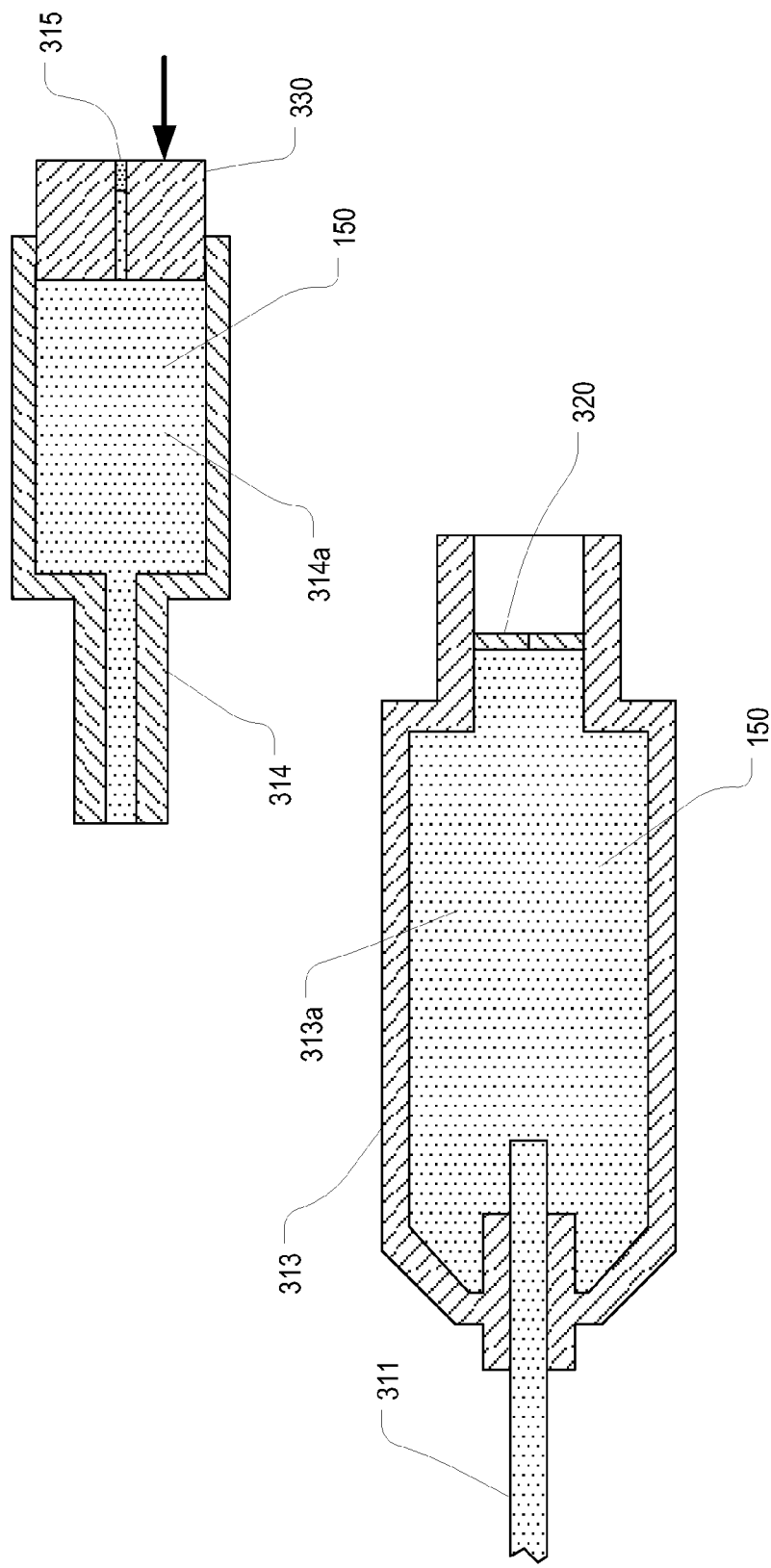

FIG. 3F illustrates an embodiment where plunger 314 also includes a plunger 330. In this embodiment, plunger 330 can be forced into reservoir 314a to cause blood to be expelled from plunger 314 (when plunger 314 is removed from proximal compartment 313) or from fluid pathway 312a (when plunger 314 is inserted within proximal compartment 313). As shown, vent 315 may be formed within plunger 330. However, one or more vents may also or alternatively be formed elsewhere on plunger 314 and/or proximal compartment 313.

As stated above, a needle tip shield in accordance with embodiments of the present invention provides a fluid pathway through which blood collected in a reservoir of a proximal compartment is expelled. This fluid pathway can be provided in two general ways. First, the fluid pathway can be the same pathway through which the distal tip of the needle is withdrawn into the needle tip shield. Second, the fluid pathway can be a different pathway from the pathway through which the distal tip is withdrawn.

Figure 4A:
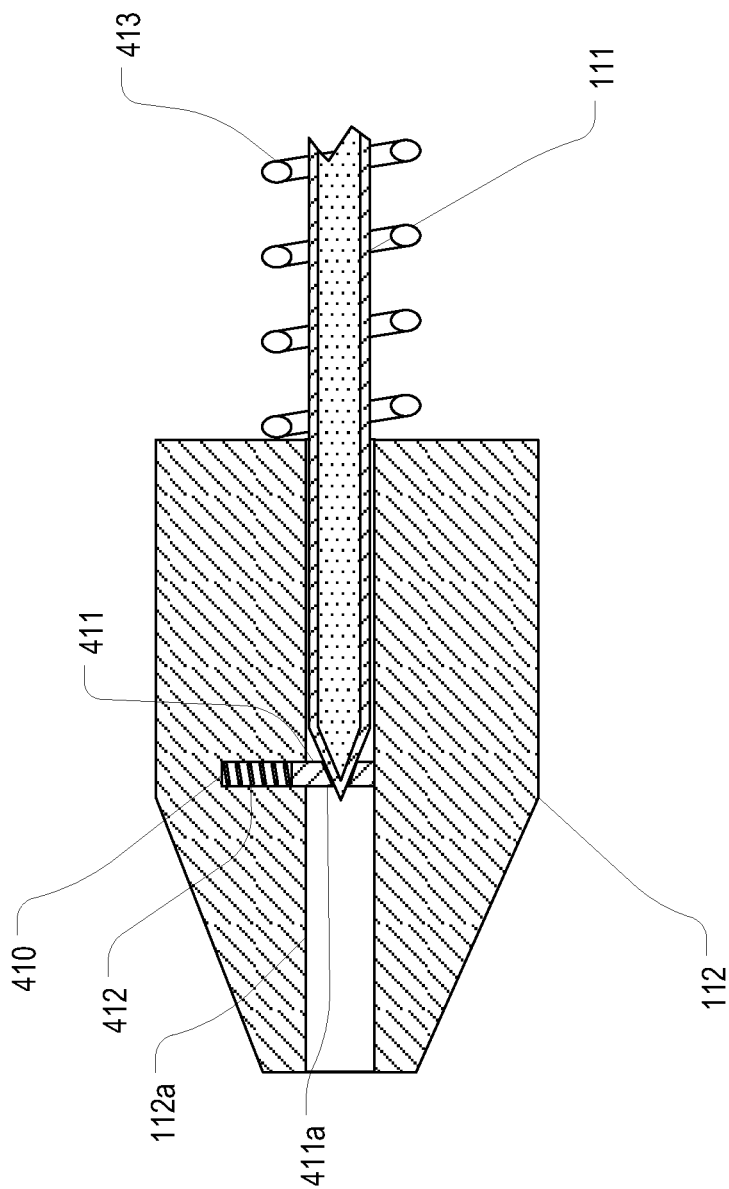
FIG. 4A illustrates a cross-sectional front view of a needle tip shield in accordance with one or more embodiments of the invention.

FIG. 4A illustrates an example of how the fluid pathway can be the same as the pathway through which the distal tip is withdrawn into the needle tip shield. FIG. 4A employs needle tip shield 112 from FIGS. 1A-1D; however, the depicted example can be employed on a needle tip shield of any of the disclosed embodiments.

In FIG. 4A, needle tip shield 112 includes a pocket 410 within which a tip guard 411 and a spring 412 are initially contained prior to actuation of the needle tip shield. Specifically, prior to distal tip 411a being withdrawn proximally past pocket 410, spring 412 will force tip guard 411 against the outer surface of needle 111. Then, once distal tip 111a has been withdrawn past pocket 410, spring 412 forces tip guard 411 into fluid pathway 112a. Tip guard 411 can include an opening 411a. In some embodiments, such as is shown, a distal-most portion of distal tip 111a may extend through opening 411a. However, in other embodiments, no portion of distal tip 111a may extend through opening 411a.

Opening 411a can serve to reduce the inner diameter of fluid pathway 112a sufficiently to prevent blood 150 from flowing out from fluid pathway 112a absent a reduction in the volume of reservoir 113a. In some embodiments, tip guard 411 may also prevent distal tip 411a from reemerging from the distal end of needle tip guard 112. As shown, needle tip shield 112 may also include a spring or other structure 413 for ensuring that distal tip 111a remains within needle tip shield 112. Spring 413 may be connected to another structure (not shown) that limits proximal movement of needle 111 with respect to needle tip shield 112 and may also apply a distal biasing force on needle 111.

Figure 4B:
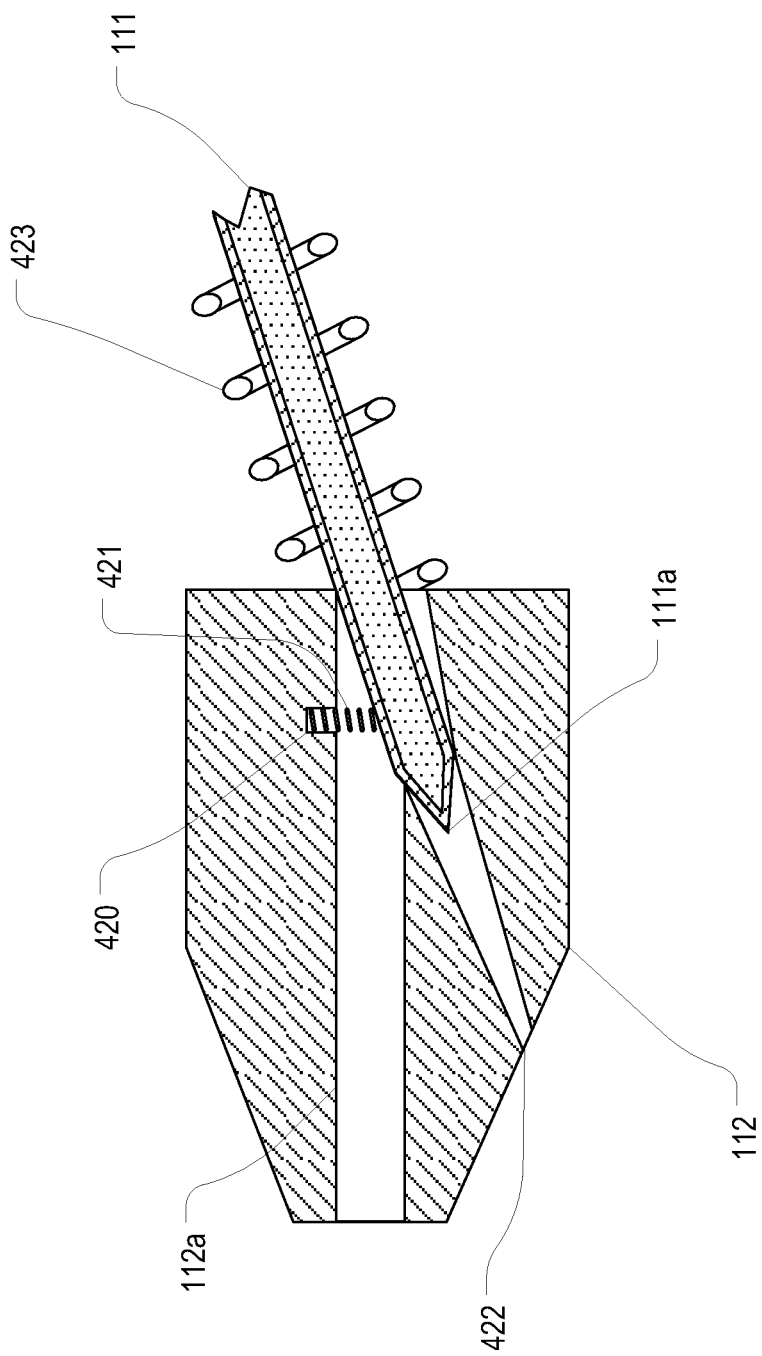
FIG. 4B illustrates a cross-sectional front view of another needle tip shield in accordance with one or more embodiments of the invention.

FIG. 4B illustrates an example of how the fluid pathway can be a different pathway than the pathway through which the distal tip is withdrawn into the needle tip shield. FIG. 4B also employs needle tip shield 112 from FIGS. 1A-1D; however, the depicted example can be employed on a needle tip shield of any of the disclosed embodiments.

In FIG. 4B, needle tip shield 112 includes a second pathway, fluid pathway 422, into which distal tip 111a is forced once it is withdrawn into needle tip shield 112. As shown, needle tip shield 112 can include a pocket 420 within which a spring 421 is contained. As with the example in FIG. 4A, spring 421 can initially force against the external surface of needle 111. Then, once distal tip 111a has been withdrawn past the proximal opening to fluid pathway 422, spring 421 will force distal tip 111a into fluid pathway 422 as shown. A spring 423 may also be employed to distally bias needle 111 thereby securing distal tip 111a within fluid pathway 422 while also preventing needle 111 from moving proximally out from needle shield 112.

Fluid pathway 422 can include a narrowed inner diameter to prevent blood flow absent a reduction to the volume of reservoir 113a. In FIG. 4B, the distal opening of fluid pathway 422 is shown as being substantially narrowed from the inner diameter of fluid pathway 422 at a proximal end.

Many other structures and techniques can be employed to secure a distal tip within a needle tip shield in addition to the examples shown in FIGS. 4A and 4B. In short, any needle tip shield that provides a fluid pathway for dispensing blood contained within a reservoir of a proximal compartment can be employed.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

The invention claimed is:

1. A needle assembly comprising:
a needle having a sharpened distal tip and an inner lumen, the needle being configured to be used within an intravenous device;
a proximal compartment coupled to a proximal end of the needle, a body of the proximal compartment forming a reservoir that is in fluid communication with the inner lumen of the needle thereby allowing blood to be withdrawn through the inner lumen and into the reservoir, wherein the body of the proximal compartment is compressible towards a longitudinal axis of the proximal compartment, wherein in response to compression of the body of the proximal compartment towards the longitudinal axis, at least a portion of the blood contained within the reservoir is expelled through the needle and a needle tip shield, wherein the proximal compartment includes a plunger, wherein in response to advancement of the plunger into the reservoir, at least a portion of the blood contained within the reservoir is expelled through the needle tip shield; and
the needle tip shield secured to the needle and configured to capture the sharpened distal tip when the sharpened distal tip is withdrawn from the intravenous device, wherein, with the sharpened distal tip captured within the needle tip shield, the needle tip shield blocks distal motion of the sharpened distal tip within the needle tip shield and the needle tip shield comprises a fluid pathway through which the blood contained within the reservoir is dispensable from the needle tip shield, wherein the needle tip shield comprises a pocket, a tip guard, and a spring, wherein the tip guard and the spring are disposed within the pocket, wherein in response to the distal tip of the needle being withdraw proximally past the pocket, the spring forces the tip guard into the fluid pathway.

2. The needle assembly of claim 1, wherein the plunger forms a second reservoir.

3. The needle assembly of claim 2, wherein the plunger includes a second plunger for reducing the volume of the second reservoir.

4. The needle assembly of claim 2, wherein the plunger is removable from the proximal compartment to enable blood contained within the second reservoir to be expelled through an opening of the plunger.

5. The needle assembly of claim 4, wherein the proximal compartment includes a seal through which the plunger is inserted, the seal sealing the proximal compartment once the plunger is removed from the proximal compartment.

6. The needle assembly of claim 1, wherein the tip guard comprises an opening.

7. The needle assembly of claim 6, wherein the distal tip of the needle extends through the opening.

8. The needle assembly of claim 6, wherein the opening is sized and configured to prevent blood from flowing out of the fluid pathway absent a reduction in volume of the reservoir.

9. A catheter assembly, comprising: a catheter adapter from which a catheter extends; and a needle assembly, comprising: a needle having a sharpened distal tip and an inner lumen, the needle extending through the catheter adapter and the catheter such that the sharpened distal tip extends distally from the catheter; a proximal compartment secured to a proximal end of the needle, the proximal compartment extending proximally from the catheter adapter, a body of the proximal compartment forming a reservoir for collection of blood via the inner lumen of the needle, wherein the proximal compartment comprises a plunger, wherein the plunger comprises a vent to facilitate flow of the blood into the proximal compartment, wherein the plunger is moveable from a proximal position to a distal position, wherein a proximal end of an exterior of the body of the proximal compartment contacts the plunger to prevent movement of the plunger beyond the distal position; and a needle tip shield secured to the needle and configured to capture the sharpened distal tip when the sharpened distal tip is withdrawn from the catheter adapter, wherein, with the sharpened distal tip captured within the needle tip shield, the needle tip shield blocks distal motion of the sharpened distal tip within the needle tip shield and the needle tip shield forms a fluid pathway aligned with a longitudinal axis of the needle and through which the blood contained within the reservoir is dispensable from the needle tip shield, wherein the body of the proximal compartment is compressible towards a longitudinal axis of the proximal compartment, wherein in response to compression of the body of the proximal compartment towards the longitudinal axis of the proximal compartment, at least a portion of the blood contained within the reservoir is expelled through the needle tip shield, wherein in response to advancement of the plunger into the reservoir, at least a portion of the blood contained within the reservoir is expelled through the needle tip shield and wherein the needle tip shield comprises a pocket, a tip guard, and a spring, wherein the tip guard and the spring are disposed within the pocket, wherein in response to the distal tip of the needle being withdraw proximally past the pocket, the spring forces the tip guard into the fluid pathway.

10. The intravenous catheter of claim 9, wherein a portion of the plunger is compressible towards a longitudinal axis of the plunger.

11. The intravenous catheter of claim 9, wherein the fluid pathway is one of:
the same pathway through which the sharpened distal tip is withdrawn into the needle tip shield; or
a different pathway than a pathway through which the sharpened distal tip is withdrawn into the needle tip shield.

12. A method of dispensing blood for point-of-care testing, comprising:
collecting blood from the patient in a proximal compartment of a needle assembly of a catheter assembly, wherein the catheter assembly comprises: a catheter adapter; and the needle assembly, comprising: a needle having a sharpened distal tip and an inner lumen; the proximal compartment secured to a proximal end of the needle, a body of the proximal compartment forming a reservoir that is in fluid communication with the inner lumen of the needle thereby allowing blood to be withdrawn through the inner lumen and into the reservoir, wherein the body of the proximal compartment is compressible towards a longitudinal axis of the proximal compartment, wherein the proximal compartment includes a plunger, wherein the reservoir inserts partially into the proximal end of the catheter adapter; and a needle tip shield secured to the needle and configured to capture the sharpened distal tip when the sharpened distal tip is withdrawn from the catheter adapter, wherein, with the sharpened distal tip captured within the needle tip shield, the needle tip shield blocks distal motion of the sharpened distal tip within the needle tip shield and the needle tip shield comprises a fluid pathway through which the blood contained within the reservoir is dispensable from the needle tip shield; and advancing the plunger into the reservoir, wherein in response to advancement of the plunger into the reservoir, at least a portion of the blood contained within the reservoir is expelled through the needle tip shield and onto a point-of-care cartridge and wherein the needle tip shield comprises a pocket, a tip guard, and a spring, wherein the tip guard and the spring are disposed within the pocket, wherein in response to the distal tip of the needle being withdraw proximally past the pocket, the spring forces the tip guard into the fluid pathway.

13. The method of claim 12, further comprising compressing the body of the proximal compartment towards the longitudinal axis such that at least a portion of the blood contained within the reservoir is expelled through the needle tip shield.

* * * * *